United States Patent
Defemme et al.

(10) Patent No.: US 9,174,777 B2
(45) Date of Patent: Nov. 3, 2015

(54) LIQUID RECEIVING BOTTLE WITH DROP BY DROP DISPENSING HEAD

(75) Inventors: Alain Defemme, Chamalieres (FR); Fabrice Mercier, Clermont Ferrand (FR)

(73) Assignee: LABORATOIRES THEA, Clermont Ferrand (FR)

( * ) Notice: Subject to any disclaimer, the term of this patent is extended or adjusted under 35 U.S.C. 154(b) by 0 days.

(21) Appl. No.: 13/576,978

(22) PCT Filed: Feb. 3, 2011

(86) PCT No.: PCT/IB2011/000182
§ 371 (c)(1),
(2), (4) Date: Aug. 3, 2012

(87) PCT Pub. No.: WO2011/095877
PCT Pub. Date: Aug. 11, 2011

(65) Prior Publication Data
US 2012/0310185 A1    Dec. 6, 2012

(30) Foreign Application Priority Data

Feb. 4, 2010 (FR) .................................... 10 00457

(51) Int. Cl.
*A61M 35/00* (2006.01)
*B65D 47/18* (2006.01)
(Continued)

(52) U.S. Cl.
CPC .............. *B65D 47/18* (2013.01); *A61F 9/0008* (2013.01); *A47J 27/21191* (2013.01); *A47J 36/06* (2013.01);
(Continued)

(58) Field of Classification Search
CPC .............. A61M 35/003; A61M 11/00; A61M 2039/267; A61M 2206/16; A61M 35/00; B01D 35/04; B01D 2313/08; A47J 27/21191; A47J 36/06; A47J 36/14; A47J 41/0088; B65D 47/06; B65D 47/18; B65D 25/40; B65D 25/48; B65D 2547/063; B65D 83/28; C02F 1/003; C02F 2201/295; G01F 11/028; G07F 17/0092
USPC .......... 604/296, 300; 222/1, 189.07, 420, 422
See application file for complete search history.

(56) References Cited

U.S. PATENT DOCUMENTS 3,382,871 A * 5/1968 Parry ....................... 128/200.18
5,417,860 A * 5/1995 Kay .............................. 210/472
(Continued)

FOREIGN PATENT DOCUMENTS

DE         904 267 C     2/1954
FR       2 770 495 A1    5/1999
(Continued)

OTHER PUBLICATIONS

International Search Report of PCT/IB2011/000182 (May 19, 2011).

*Primary Examiner* — Tatyana Zalukaeva
*Assistant Examiner* — Andrew J Mensh
(74) *Attorney, Agent, or Firm* — Millen, White, Zelano & Branigan, P.C.

(57) ABSTRACT

The invention relates to a bottle for packaging a liquid with dropper delivery comprising a reservoir with an elastically deformable wall that can be reversed by letting air into the receptacle, surmounted by a dispensing head for the liquid comprising a drop-counting end-piece protruding to the outside of the bottle and an anti-bacterial filtering membrane, made partially hydrophilic and partially hydrophobic, which is interposed across the path of the liquid and of the air, at the base of the said end-piece. The dispensing head comprises an insert with a recessed body which contains a porous pad regulating the flow of liquid placed downstream of the reservoir and upstream of a chamber delimited downstream of the said membrane. At the base of this insert on the inner side of the bottle, longitudinal arches supporting a central pellet make star-shaped passageways radially guiding the air that enters the bottle after having passed through the porous pad.

13 Claims, 2 Drawing Sheets

(51) Int. Cl.

| | | |
|---|---|---|
| *A61F 9/00* | (2006.01) | |
| *B67B 7/00* | (2006.01) | |
| *B67D 7/76* | (2010.01) | |
| *G07F 17/00* | (2006.01) | |
| *C02F 1/00* | (2006.01) | |
| *B65D 25/40* | (2006.01) | |
| *B65D 25/48* | (2006.01) | |
| *A47J 36/06* | (2006.01) | |
| *B65D 47/06* | (2006.01) | |
| *B01D 35/04* | (2006.01) | |
| *B65D 83/28* | (2006.01) | |
| *A47J 36/14* | (2006.01) | |
| *A47J 27/21* | (2006.01) | |
| *A61M 39/26* | (2006.01) | |
| *A61M 11/00* | (2006.01) | |
| *G01F 11/02* | (2006.01) | |
| *A47J 41/00* | (2006.01) | |

(52) U.S. Cl.
CPC ............... *A47J 36/14* (2013.01); *A47J 41/0088* (2013.01); *A61M 11/00* (2013.01); *A61M 35/00* (2013.01); *A61M 35/003* (2013.01); *A61M 2039/267* (2013.01); *A61M 2206/16* (2013.01); *B01D 35/04* (2013.01); *B01D 2313/08* (2013.01); *B65D 25/40* (2013.01); *B65D 25/48* (2013.01); *B65D 47/06* (2013.01); *B65D 83/28* (2013.01); *B65D 2547/063* (2013.01); *C02F 1/003* (2013.01); *G01F 11/028* (2013.01); *G07F 17/0092* (2013.01)

(56) References Cited

U.S. PATENT DOCUMENTS

| | | | | |
|---|---|---|---|---|
| 5,845,814 | A | * | 12/1998 | Nobbio .................. 222/129 |
| 6,336,571 | B1 | | 1/2002 | Chibret et al. |
| 7,971,755 | B2 | | 7/2011 | Faurie |
| 2002/0153386 | A1 | * | 10/2002 | Uetake et al. ................ 222/1 |
| 2008/0067194 | A1 | | 3/2008 | Faurie |
| 2010/0116852 | A1 | * | 5/2010 | Painchaud et al. ............ 222/422 |

FOREIGN PATENT DOCUMENTS

| | | |
|---|---|---|
| FR | 2 872 137 A1 | 12/2005 |
| WO | WO 95/28335 A1 | 10/1995 |

\* cited by examiner

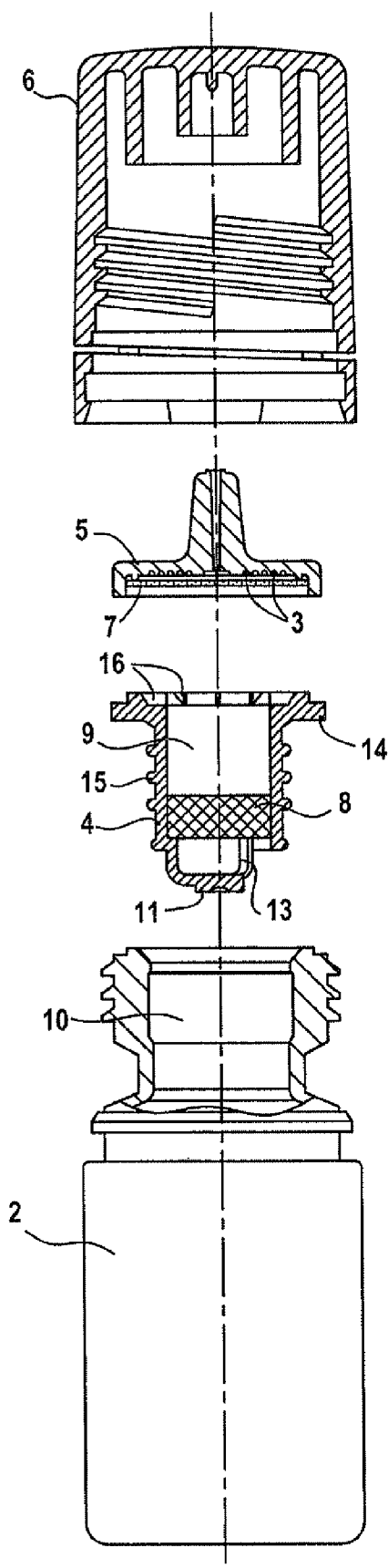
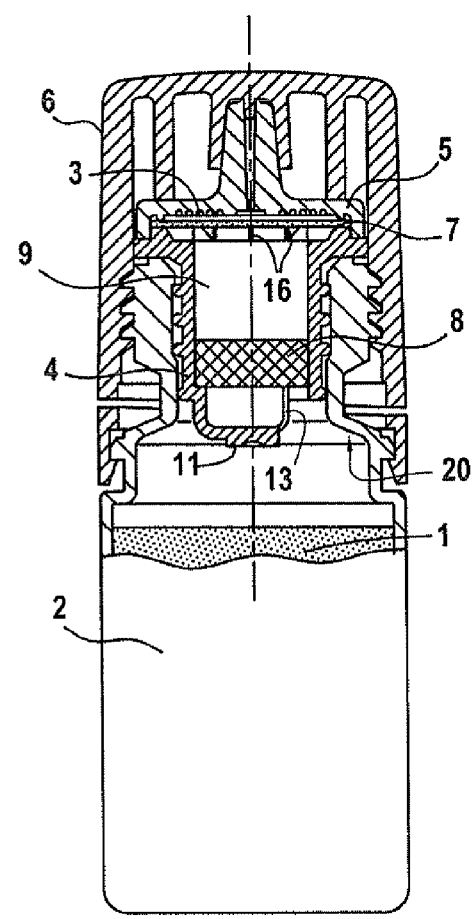
FIG. 1
FIG. 1A

LIQUID RECEIVING BOTTLE WITH DROP BY DROP DISPENSING HEAD

The present invention relates to the design and production of a receptacle for packaging and for controlled delivery of a liquid. In the context notably of a destination for drop-by-drop delivery, its main novel features relate to the top for delivering the liquid from the reservoir of a bottle with an elastically deformable wall that can be reversed returning to its initial conformation by aspiration of air into the bottle after delivery of a dose of liquid.

The invention applies preferably but not restrictively to the field of pharmaceutical liquid compositions, notably in the ophthalmological applications. This is a field in which the questions of purity of the delivered product and accuracy of delivery are particularly important. Very similar requirements may be found, for example, in cosmetology or dermatology, notably with respect to accuracy in the location to which the expelled drop is conveyed, if necessary concerning compliance with a predetermined administration dose.

More particularly, the subject of the invention is a packaging bottle with a reservoir with an elastically deformable wall that is reversible and with a top for delivering liquid through a drop-counting end-piece protruding to the outside of the bottle which comprises an anti-bacterial filtering membrane protecting the liquid contained in the reservoir from polluting agents from the outside environment. In bottles manufactured industrially by the Applicant, in compliance notably with the French patent application published under No. FR 2 872 137, such a membrane is placed between the reservoir for liquid inside the bottle and the delivery end-piece, at the base of the channel for expelling drops, across a duct for the flow of liquid, and it is this same duct which also serves as the entrance for the outside air coming to reinflate the bottle replacing the previously expelled liquid, after each delivery operation.

This operation is made possible by using as an antibacterial filtering membrane a bifunctional membrane, partially hydrophilic and partially hydrophobic, like those that can be produced for example in polyethersulphone-based polymer. The distinctive feature of these membranes is that they allow themselves to be traversed alternately either preferably by the aqueous liquid of the bottle, or preferably by the air from the outside, depending on a pressure differential between the pressure existing on the side of the membrane oriented towards the reservoir and the pressure existing on the opposite side of the membrane oriented towards the delivery channel.

The presence of such a membrane, allowing on the one hand the liquid to pass in the delivery direction under the effect of a pressure exerted by the user on the wall of the reservoir, and, on the other hand, the passage of the air in the reverse direction, from the outside to the reservoir, when the pressure on the bottle is relaxed after the delivery of a drop of liquid, is one of the factors that make it possible to package ophthalmic liquids in multi-dose bottles without it being necessary to incorporate preservatives in their composition.

But the correct operation of the multi-dose bottles thus formed requires a precise control of the production of the drops which, in the bottles produced by the Applicant and as described in the patent already cited, requires the use of a dispensing head having, across the flow of the liquid between the reservoir and the membrane, an insert with a recessed body containing a porous (more precisely microporous) pad which acts as a regulator of the flow of liquid. The pad is therefore placed downstream of the reservoir in the direction of flow of the liquid from the reservoir to the delivery end-piece, and upstream of the bifunctional membrane. Advantageously it is made of a material with hydrophobic properties.

The use of such bottles, although it is satisfactory in many cases, nevertheless poses specific problems of drop-by-drop operation when it involves packaging solutions having surface-active properties. This is so to such a point that, in this case, in order to avoid recourse to preservative agents, single-dose packaging ampoules are preferred to them, despite their drawbacks in terms of consumption of product (excess content remaining wasted with each use). The problem of the bad quality of formation of the drops is encountered notably for ophthalmic formulations containing either active principles that per se have surface-active properties, or surface-active additives used as emulsifying agents (for example polysorbate, glycerol, polyethylene glycol ricinoleate), or else other excipients, like certain viscosing or lubricating agents of the family of the polyvinylic derivatives or that of the polyethylene glycols.

At the origin of the invention, it appeared that the drop-by-drop delivery in such situations can be hampered by the fact that foam forms on leaving the porous pad and that the operation of the hydrophilic/hydrophobic bifunctional membrane is disrupted when a biphase liquid/gas mixture can make contact with it.

To solve the problem and achieve substantially the same effectiveness in drop-by-drop delivery as has been seen in the case of non-foaming liquids, efforts were then made to work no longer on the conditions of flow of the liquid when it is expelled from the bottle, but rather on the conditions in which air enters after each delivery operation. It is in this way that a form of construction of the dispensing head was achieved which tends to prevent the retention of air inside the porous pad, the air remaining in the pad with each passage being made responsible for the formation of foam in the liquid which then passes through the pad in the reverse direction.

According to the invention, the proposal is to form the insert of the dispensing head, which by the periphery of its main body is mounted sealingly in the neck of the reservoir, with a base extending the said body beyond the porous pad which enters the inside of the bottle, therein making air passageways in a star pattern which guide the air radially to the periphery of the bottle. While promoting the attraction of air extracted from the porous pad, by virtue of a section of passageway that is wide open causing no loss of pressure in this location, such passageways have the effect of distributing the air uniformly over the whole section of the bottle, above the surface of the liquid still contained in the reservoir. It is advantageous that, in addition, the same base of the insert forms, beyond these radial passageways, a central pellet forming an obstacle to a blast of air directly to the surface of the liquid in the general axis of revolution of the bottle.

In addition to the foregoing, the invention advantageously provides that, in the main body of the insert, the porous pad is at a distance from the bifunctional membrane by an axial height allowing any air bubble leaving the pad complete latitude to burst before reaching the membrane, even in the case of a formulation with surface-active properties. This prevents any risk of formation of foam in the expelled drop. It ensures that at the time of extraction of a drop, the membrane is covered with a film of liquid containing no air. It will be noted that the hydrophobic portion of the membrane then represents the critical point, because, surface areas being equal, the flow rate of air on the hydrophobic portion is much greater than the flow rate of liquid of the hydrophilic portion. In a formulation with no surface-active property, the air bubbles burst instantaneously as soon as they form on leaving the porous pad under the effect of the pressure exerted on the body of the bottle. On the other hand, a foaming solution promotes the creation of bubbles of larger size the particular feature of which is that they can deform before being able to burst, which gives them a longer lifetime inside the dispensing head.

By avoiding the disruptive effects of a biphase mixture in the expelled liquid and the consequences of a malfunction of the bifunctional membrane, the invention makes it possible to ensure the reproducibility of the volume of liquid in each drop of the liquid delivered on each delivery operation and the composition of this liquid. There are two essential factors for the prescribed administration dose to be observed by a patient in the case of ophthalmic drops. These advantages provided by the invention are obtained while preserving the conditions of correct operation that are associated with the conditions of flow of the liquid, all the more so when working on the air flow at its entry into the reservoir inside the bottle, therefore upstream of passing through the porous pad in the direction of flow of the liquid.

More precisely, the bottle according to the invention, designed for the packaging of a liquid to be delivered drop-by-drop, advantageously has the particular features set out below, to be considered separately or in any technically achievable combination. It comprises a reservoir with an elastically deformable wall that can be reversed by letting air into the said reservoir through a delivery head through which the liquid is delivered under the effect of a pressure exerted against the said wall, the said delivery head comprising an insert with recessed body, by which it is mounted in a sealed manner in the neck of the bottle, in communication with the said reservoir. This delivery head comprises an end-piece extending it to the outside of the bottle that is pierced with a central channel leading to an orifice for the expulsion of the liquid. It also comprises an anti-bacterial filtering membrane, made partially hydrophilic and partially hydrophobic, which is mounted on the base of the said end-piece, between the latter and the said insert. It allows through it the passage of the liquid in the direction of delivery and the passage in the opposite direction of the air required to enter the bottle in compensation after a delivery of liquid. The insert contains a porous pad regulating the flow on the path of the liquid pushed from the reservoir to the expulsion channel (when there is a reduction in the internal volume under the effect of the pressure exerted manually on the wall of the bottle). This pad advantageously made of a hydrophobic material is placed across the duct formed by the central recess of the pad, in an axial position downstream of the reservoir and upstream of a chamber which is itself delimited downstream by the filtering membrane placed upstream of the end-piece. "Upstream" and "downstream" are defined in this instance with respect to the direction of flow of the liquid when it is delivered, that is to say from the packaging reservoir to the channel for expelling the drops.

According to the invention, the insert with a recessed body advantageously ends, at its end directed towards the reservoir, in a seat formed by longitudinal arches supporting a central pellet with a diameter smaller than the internal diameter of the insert, at a distance from the internal periphery of the bottle at its internal space forming the reservoir receiving the liquid at rest. Its shape leaves a considerable open space for the passage of the liquid leaving the reservoir to the dispensing head, and above all it makes wide open passageways in the bottle in the radial direction, which makes it easier for the compensating air to enter that is sucked through the porous pad between two liquid-expulsion operations, while distributing it immediately over the whole section of the bottle, including in the vicinity of its peripheral wall.

The arches of the base of the insert advantageously take the shape of longitudinal lugs which fold radially at their bottom end to support the central pellet and to connect it to the external ring of the body. Such a shape gives the insert good strength against the compression at its base. It provides a good mechanical strength to the insert in the longitudinal direction preventing buckling. It makes it possible to guide this assembly, while giving mechanical strength, when it is put in place by insertion into the neck of the bottle by longitudinal pressure along the axis of the neck. It also makes it possible to retain the porous pad which might slide towards the reservoir of the bottle during handling. Also, it helps to provide the individualization of the elements of an assembly of dispensing heads during their storage and their transport when they are bagged in bulk before they are fitted into the bottles. The space requirement of the insert bases (arches and central pellet) prevents two dispensing heads being linked together by penetration of an end piece of one into the central duct of the insert of the other, and thus prevent any stresses that would arise, in the industrial manufacture of collyria of having to separate the tops that have thereby become stuck to one another.

The bottle furnished with a dispensing head according to the present invention is extremely advantageous in terms of regulating flow and of controlling the volume of drops expelled, because of the particular structure of the seat of the insert placed in the neck of the reservoir and containing the flow-regulating microporous pad. Such a structure notably allows an easy return of the air into the reservoir for storing the liquid, at a distance from the membrane, after each delivery operation. This evening out of the flows of air and of liquid reduces the quantity of air bubbles in the liquid which flows out to the membrane when drops of liquid, notably surface-active liquids, are delivered. Moreover this gives, for the intermediate chamber between the porous pad and the membrane, an appropriate distance necessary for the bursting of the air bubbles which may be present at the interface of the exit from the pad when the flow of liquid brings air with it that has remained absorbed within the pad between two expulsion operations. It is possible to consider that this chamber has, for the exiting liquid flow, a role as a flow-rate-regulating pad complementing that of the material pad, and a distributing role in the transverse direction before passing through the membrane if the latter has an even distribution of the hydrophilic zones and hydrophobic zones. Moreover, since the said chamber forms an air cushion, it also plays a cross-sectional distribution role when operating on the entry of air between the end-piece which lets the air in and the external face of the material pad, which promotes good conditions of air entry. It promotes the delivery of even doses of liquid. This chamber also, as is already known, keeps the membrane dry between two delivery operations, when the receptacle rests in its normal position, that is to say resting on its base, receiving inside it the unexpelled residual liquid.

According to embodiments preferred in industrial practice, the invention also satisfies the following features applied separately or in each of their technically feasible combinations.

According to one advantageous feature of the invention, the arches are three in number, placed at equal distances from one another so as to open wide the passageway section provided for the air entering the bottle, while providing a good firmness to the base of the insert body.

For the same purpose of preventing any loss of pressure on the air flow entering the bottle, in preferred embodiments of the invention, the arches have a height of between 1 and 5 mm, in particular between 2 and 4 mm.

The hydrophobic microporous pad situated in the body, the whole section of which it occupies, and through which a loss of pressure is created, regulates the liquid flows. In this way it promotes the controlled delivery of the doses of liquid. It also prevents the liquid contained in the reservoir from flowing when no pressure is applied to the wall of the latter.

According to one advantageous feature of the invention, the pad is designed to trap the minimum of air in its pores.

The porosity of this pad is suitable for the entering flow (air) and exiting flow (liquid) so as not to cause too great a pressure loss and must also ensure an adequate size for the air bubbles so that they can burst easily before reaching the surface of the membrane.

Therefore, in preferred embodiments of the invention, the hydrophobic microporous pad has an equivalent porosity of between 20 and 120 µm.

The pad is preferably made of low-density polyethylene which gives it a hydrophobic property so that it is not absorbent. Its microporous property nevertheless allows the liquid to pass through it, under the effect of a sufficient pressure differential, induced between the reservoir and the outside by the pressure applied by the user to its deformable wall. Its nature is such that it does not interact with the formulation of the liquid, more particularly with the active principle.

In order to obtain the chamber height (distance between the top face of the pad and the membrane) necessary for the air bubbles to burst before they reach the membrane, it is possible to work on the longitudinal thickness (height) and/or the arrangement of the pad.

According to one advantageous feature of the invention, the pad has a longitudinal thickness that is big enough to form a pressure loss capable of preventing the liquid from wetting the membrane before the first use of the bottle, in order to prevent the deterioration of the latter, while being small enough to ensure that the chamber arranged between it and the membrane has a considerable height. Therefore, when the bottle is used, the bubbles that can form on the top surface of the pad, that is to say the surface directed towards the chamber, have all the room to burst inside the chamber without risking reaching the bifunctional membrane. The latter is therefore saved from these air bubbles.

According to a preferred embodiment of the invention, the height of the chamber, that is the distance between the top face of the porous pad and the membrane, is greater than 2 mm. Preferably it is greater than or equal to approximately 3 mm. Again preferably it has a value of between 4 and 10 mm, notably between 5 and 9 mm.

The longitudinal thickness of the pad, once inserted into the insert, ranges preferably between 0.3 and 0.8 mm. The pad is compressed when it is put in place in the recessed body and its thickness can be reduced by 50%. It is placed in the insert so that the chamber that surmounts it downstream (in the direction of flow of the liquid) is high enough, as defined above, to allow the air bubbles that may form in the liquid leaving the pad to burst before reaching the membrane.

The bifunctional membrane is conventional per se. It is for example made of polyamide-resin-based or polyethersulphone-resin-based polymers. It is given a basic hydrophilic property, so as to selectively allow the liquid to pass through it during the delivery operation. It is made partially hydrophobic on a portion of its surface, which then selectively allows air to pass from the outside to the reservoir after each delivery operation, by modification of its structure, notably by grafting in the presence of a radical reaction initiator. This treatment is notably carried out on a middle band occupying 20 to 50% of its surface placed across the path of the liquid. The membrane also preferably has an average pore diameter of the order of 0.1 to 0.2 µm in order to play an anti-bacterial role by filtration protecting the liquid still present in the bottle from any biological contamination coming from the outside.

According to one advantageous feature of the invention, the insert with a recessed body is designed to be able to be forced into the neck of the bottle by a pressure on a longitudinal axis. It is preferably assembled inside the receptacle by tight-contact fitting.

The central pellet supported by the arches at a distance from the main portion of the insert is advantageously useful for providing a strength during the insertion, made by force, of the insert into the neck of the receptacle when the latter is produced. It is very useful when the method for producing the insert is made by plastic injection, because it makes it possible to position the injection point at its level and to prevent sealing problems that would be posed by moulding flashes situated on the periphery of the insert body.

In preferred embodiments of the invention, the insert body is elastically deformable at its periphery to make it easier to put in place by being forced into the neck of the receptacle. It comprises on its top edge a ring of larger diameter resting against the top edge of the neck of the receptacle, so as to ensure a good positioning of the insert in the neck. During assembly, this ring advantageously also serves as a bearing surface for pushing the insert into the neck.

The insert is preferably fitted on its outer surface with at least one o-ring, preferably with a plurality of o-rings axially distributed ensuring that the contact between the insert and the neck of the receptacle is sealed. These o-rings, called flutes, notably form a one-piece assembly with the insert.

The insert, like the other elements forming the receptacle according to the invention, are preferably advantageously manufactured by moulding, and then assembled together.

The receptacle according to the present invention also provides advantages as they may have been described in the patents of the Applicant and notably of the patent published under No. FR 2 872 137, associated with the presence of a reservoir with a reversibly deformable wall, of an anti-bacterial filtering membrane, of a flow-regulating pad and of a chamber inserted between these latter two elements. In particular, the reversibly deformable wall ensures optimum use of all the liquid contained in the reservoir: the latter retains intact an expulsion capability throughout the successive delivery operations, by virtue of letting in air which returns the expulsion pressure to its initial value after each expulsion operation. The membrane protects the liquid contained in the reservoir from outside contamination. It also constitutes a cause of pressure loss which is added to that generated by the microporous pad in order to improve the regulation of the flow of liquid and in order to ensure that there are no leaks from the reservoir when no pressure is applied to the wall of the latter.

In addition to its effectiveness in terms of controlling the volume of liquid delivered, of conserving the liquid in the reservoir and of optimizing the use of the total volume of liquid, the receptacle according to the invention also has the advantages of a simple structure, a production cost that is limited and totally appropriate to the field of application of the products that can be consumed, to be thrown away after use, and a great ease of use for the consumer.

As indicated, the invention applies more particularly to a bottle used for the packaging and delivery of a liquid containing compounds having surface-active properties, in particular a collyrium.

The invention may find application in all fields in which drop-counter bottles are used, more particularly in any situation in which the product to be delivered is a foaming product containing a compound having surface-active properties promoting the formation of air bubbles.

The invention also relates to the dispensing head as described above designed to be fitted to elastic-walled reservoirs of drop-counter bottles.

BRIEF DESCRIPTION OF THE DRAWINGS

The invention will now be more fully described in the context of preferred features and their advantages, by making reference to FIGS. 1 to 3 in which:

FIG. 1 represents in axial section a bottle according to the invention;

FIG. 1A represents in exploded axial section the bottle of FIG. 1;

Figure 2:
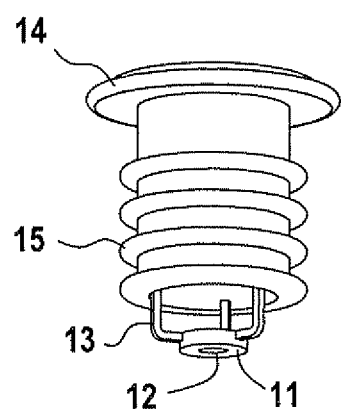
FIG. 2 illustrates the recessed-bodied insert of the dispensing head of the bottle of FIG. 1, in a perspective view.

A receptacle for packaging a liquid to be delivered drop-by-drop is illustrated in FIGS. 1 and 1A in the form of a bottle designed more particularly for the packaging of a collyrium. Its elements generally consist of a plastic compatible with the application in order to conserve an ophthalmic solution. They are notably each made of a polymer of the family of polyethylenes.

The bottle comprises a liquid-storage reservoir 2 the cylindrical peripheral wall of which is reversibly elastically deformable, to allow delivery of the liquid 1 based on a manual compression applied to it by the user, then a spontaneous return to its initial shape by letting air in when this compression is relaxed. The entrance of air in compensation for each drop of expelled liquid takes place on a reverse path of this expulsion through the dispensing head occupying the neck of the bottle. No other entry of air is possible; in particular, there is no pressure-balancing hole through the wall of the bottle and the base of the neck. The cylindrical peripheral wall has, at its free end, a narrowing portion 20 which is extended by a neck 10.

The dispensing head for delivering the liquid drop-by-drop comprises a recessed-bodied insert 4 placed inside the neck 10 of the bottle, a delivery end-piece (or nozzle) 5, and optionally, as here, a removable cap 6 for closing off the end-piece, which is conventionally strewn around the neck of the bottle. It also comprises a microporous pad 8 included in the insert 4 and an anti-bacterial membrane 7 placed at the base of the end-piece 5.

The anti-bacterial filtering membrane 7, partially hydrophilic and partially hydrophobic, is placed upstream of the end-piece 5, in the direction of flow of the liquid from the reservoir to the delivery end-piece, in order to protect the liquid 1 by filtration of the external contaminations, notably bacteria. This membrane 7 is freely supported in operation by being pressed against the seat of the end-piece 5. It is attached on its periphery by heat-sealing between a peripheral ring of this seat (which here has a swelling which reduces during the sealing operation between the two parts) and an interacting bearing surface on the terminal face of the insert 4. It is made for example of polyethersulphone made partially hydrophobic on a portion of its surface. It has a porosity of the order of 0.1 to 0.2 µm. The seat of the end-piece has the shape of a recessed disc which is fitted into the recessed body 4; it comprises on its inner face microchannels 3 which make it easier for the liquid to drain towards the expulsion orifice.

The insert 4 has a generally cylindrical shape, in this instance with an internal diameter of approximately 1 cm, which opens out in its top terminal portion to reach a diameter of approximately 1.5 cm to form the interacting bearing surface which is furnished with fins 16 to support the membrane 7 when it is pressed between the insert and the end-piece. In this example, it has a height of approximately 1.5 cm in its main body (in the base formed by the arches and the pellet). It houses in its inner recess a microporous pad 8, of cylindrical shape closely conforming to that of this recess, which is made of a hydrophobic material. It is notably made of a felt with a polyethylene filling. By its presence it has the effect of regulating the flow of liquid delivered and of preventing the liquid from passing from the reservoir 2 to the end-piece 5 if there is no compression of the wall of the receptacle, and in order to regulate the flow of delivered liquid. This pad 8 is placed upstream of and at a distance from the membrane 7, in the direction of flow of the liquid from the reservoir to the delivery end-piece, so as to arrange between it and the latter an intervening chamber 9. The chamber 9 notably allows the air bubbles of the delivered liquid to burst before reaching the membrane 7. It also makes it possible to collect the residual liquid that has not been expelled.

The pad 8 has an equivalent porosity of approximately 100 µm. It also has a height, in this instance of approximately 0.5 cm in the compressed state when it is in place in the insert 4, namely equal to approximately 33% of the height of the insert body. Before being inserted therein, the pad has a height of approximately 1 cm. It is placed in the bottom portion of the insert body so that the chamber 9 arranged between it and the membrane 7 has a considerable height, in this instance of approximately 6 mm. The air bubbles that may be trapped in the pad after aspiration of air following an operation to expel a drop of liquid, have a size such that, when they are ejected from the pad during a subsequent operation of delivering liquid, at the same time as the liquid, they burst in the intervening chamber 9 before reaching the bifunctional membrane.

The insert 4 comprises at its base, at the end directed towards the inside of the reservoir containing the liquid, as illustrated in greater detail in FIG. 2, a central pellet 11 with a diameter much smaller than the diameter of the main cylindrical portion of the insert, in this instance approximately 0.4 cm. This pellet is supported by the longitudinal arches 13. These arches are in the form of lugs that are relatively long and specifically oriented in the longitudinal direction, which join together at one end of the cylindrical portion of the insert 4, and which, at their opposite end, curve radially towards the axis of the insert so as to support the pellet 11 centred on this axis.

The arches 13 are high enough to arrange between them wide open passageways for the flow of the air entering the reservoir of the bottle through the axial duct of the dispensing head. This height is notably approximately equal to 3.5 mm. The lugs that form the arches each have a total length of approximately 5 mm. The arches provide a space at the base of the insert with a volume of approximately 0.40 $cm^3$, from whence the air escapes mainly in the radial direction all around the axis of the assembly. It will be understood that it is important that the passageways formed between the arches allow on the one hand the liquid to flow from the reservoir to the outside via the pad so that the base does not hamper the delivery of liquid, and that these passageways on the other hand make it possible to orient the returning air towards the walls of the reservoir. Therefore, the returning air is oriented radially onto the walls and not directly onto the liquid that is still present in the reservoir. For this purpose the central pellet has the shape of a disc, the diameter of which is sufficiently large to block the axial passage of air originating from the pad and thus direct the air entering the reservoir towards the walls of the latter. As can be seen in FIG. 1, it is particularly advantageous that, when the insert is mounted in the neck of the bottle, the central pellet is placed at the level of the narrowing portion 20 of the bottle in which the peripheral wall is not essentially vertical. The entering air which is diverted radially after the obstruction of the pellet reaches this inclined portion of the peripheral wall of the bottle, so that the entering air does not impact the wall head on but is guided in a laminar flow along this wall towards the liquid that is still present in the reservoir.

Figure 3:
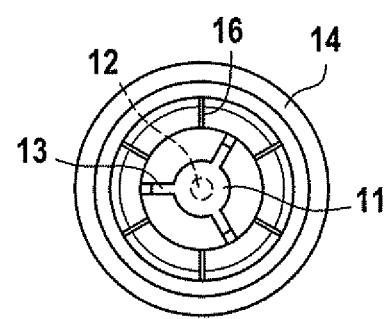
FIG. 3 shows the insert of FIG. 2 in a top view.

As can be seen in FIG. 3, the arches 13 are three in number and placed equidistantly from one another so as to ensure the firmness of this portion of the insert, notably in terms of resistance to compression in the longitudinal direction. It will be understood that the number of arches and their arrangement may be different when they arrange open passageways for the flow of liquid for its expulsion and for the return flow of air.

The central pellet 11 makes it easier to force the insert into the neck 10 of the bottle. It comprises at its centre, on its outer face, a spot 12 resulting from the point of injection of the polymer to form the assembly. The central pellet acts as an abutment when the insert is inserted into the neck of the bottle, while making it possible with the arches to ease the axial guidance of this insert. It prevents damaging and removing the porous pad during the bulk transfer of the dispensing heads furnished with their end-piece. Its presence is also useful as part of the preferred method for producing the insert, by injection moulding. It comprises at 12 the trace of the point of injection of the polymer into the mould. This prevents an injection point that might be on an external side of the insert from being able to create a leakage point that is prejudicial to the necessary seal between the insert and the neck of the bottle.

Formed on the top edge of the insert 4 is a peripheral ring 14 of larger diameter, in this instance of approximately 2 cm. This ring acts as an abutment allowing an appropriate positioning of the insert 4 in the neck 10 of the bottle during assembly.

During assembly, the insert 4 is assembled by being force-fitted into the neck 10 of the bottle. This is made possible by the light elastic deformation capacity of the material forming the insert. This fitting is achieved by means of circular o-rings 15, called flutes, arranged on the periphery of the insert. These seals are preferably made in one piece with the insert in the same production step by moulding. They ensure the contact seal with the inner wall of the neck 10. They also provide guidance of the insert at the time of assembly by axial pressure, so as to generally result in a tight contact-fitting with no risk of slanted positioning.

The bottle described according to the invention is tested with a dabbed solution comprising an emulsified active principle in an emulsifying agent having surface-active properties in order to verify the evenness of calibration of the drop of solution expelled depending on the height of the chamber, for a given insert and a given porous pad configuration meeting the specifications indicated above. The evenness of calibration of the drop is verified by weighing ten expelled drops and by repeating each test three times. These tests show that, for a chamber having a height of at least 3 mm, the variation in the volume of the expelled drop is less than 10%, which remains a sufficient quality in practice in most situations. For a height of 6 mm, the results are even better, with a variation of less than 50%.

The foregoing description clearly explains how the invention makes it possible to achieve the objectives that it set itself. In particular, it provides a receptacle for packaging and delivering a liquid, notably an ophthalmic liquid, of the type with air intake and with bifunctional filtering membrane, which ensures good evenness of delivery while notably preventing the presence of air in the delivered drops even if the liquid has surface-active properties. The invention makes it possible to control the correct calibration of the drop and the repeatability of the delivered dose in order to ensure the correct efficacity of the medicine and the absence of side effects which might be caused by an inappropriate dose. But naturally the invention is not limited to the embodiments that have been specifically described and on the contrary it extends to any variant achieved through equivalent means.

The invention claimed is:

1. Drop dispensing bottle comprising:
    a reservoir with an elastically deformable wall that can be reversed by letting air into said reservoir through a dispensing head, wherein the dispensing head includes
    an insert with a hollow body and having a base,
    a delivery end-piece as an extension of said body that is pierced with a central channel leading to an expulsion orifice, and
    an anti-bacterial filtering membrane partially hydrophilic and partially hydrophobic that is mounted across said insert at the basis of said delivery end-piece in order either to allow the passage of a liquid in the direction of delivery or to allow, in the reverse direction, the passage of air required to enter in compensation after a delivery of liquid,
    said insert containing a porous pad regulating the flow of liquid passing through it in the direction of said membrane,
    wherein the base of the insert ends beyond said pad, on the side opposite to the delivery end-piece, with a cylindrical portion forming longitudinal arches, an end of which opposite to said insert being curved radially towards an axis of the insert for supporting a central pellet centered on the axis which make between them, passageways open to a radial flow of the entering air leaving the drop dispensing head,
    through which the liquid is delivered under an effect of a pressure applied against said wall, in which said dispensing head is mounted in a sealed manner by the insert in a neck of the bottle, in communication with said reservoir, and in which the anti-bacterial filtering membrane, partially hydrophilic and partially hydrophobic, is mounted across said insert at the basis of said delivery end-piece, in order to allow the passage of the liquid in the direction of delivery and, in the reverse direction, the passage of air required to enter the bottle in compensation after a delivery of liquid, characterized in that the base of the insert is located beyond the neck of said reservoir and ends inside said reservoir with arches providing passageways for a radial circulation of the air entering the bottle through said pad to the periphery of the reservoir,
    wherein the central pellet is level with a narrowing portion inclined toward a periphery of the reservoir.

2. Drop dispensing bottle according to claim 1, characterized in that said central pellet is a shape of a disc centred in the axis of the insert so as to leave an open space for the passage around it of the air arriving from the dispensing head while forming an obstacle to a direct axial jet leaving the insert.

3. Drop dispensing bottle according to claim 1, characterized in that the arches are three in number, placed angularly at equal distances from one another about the axis of the insert.

4. Drop dispensing bottle according to claim 2, characterized in that the arches have a height of between 1 and 5 mm.

5. Drop dispensing bottle according to claim 2, characterized in that the porous pad is a microporous pad made of hydrophobic material in the form of a felt having an equivalent pore diameter of between 20 and 120 μm, which is made of low-density polyethylene.

6. Drop dispensing bottle according to claim 2, characterized in that the distance between a top face of the porous pad and the membrane is greater than 2 mm, and in that the distance between the top face of the porous pad and the membrane is between 4 and 10 mm.

7. Drop dispensing bottle according to claim 1, characterized in that the outer surface of the insert is fitted with a plurality of axially distributed o-rings.

8. Bottle according to claim 1, characterized in that the insert is assembled in the bottle by force-fitting inside the neck of the bottle and in that it comprises on its top edge a ring of larger diameter resting against the top edge of the neck of the bottle so as to ensure a good positioning of the said insert in the said neck.

9. Bottle according to claim 1, characterized in that the central pellet is a shape of a disc centred in the axis of said insert so as to leave an open space for the air to pass radially to the peripheral wall of the bottle while forming an obstacle to a direct axial jet leaving the insert.

10. Bottle according to claim 1, characterized in that it is used for the packaging of a liquid containing compounds having surface-active properties, in particular a collyrium.

11. Drop dispensing bottle comprising:
  a reservoir with an elastically deformable wall that can be reversed by letting air into said reservoir through a dispensing head, wherein the dispensing head includes
    an insert with a hollow body,
      a delivery end-piece as an extension of said body that is pierced with a central channel leading to an expulsion orifice, and
      an anti-bacterial filtering membrane partially hydrophilic and partially hydrophobic that is mounted across said insert at the basis of said delivery end-piece in order to allow the passage of a liquid in the direction of delivery and, in the reverse direction, the passage of air required to enter in compensation after a delivery of liquid,
    said insert containing a porous pad regulating the flow of liquid passing through it in the direction of said membrane,
    wherein the insert ends beyond said pad, on the side opposite to the delivery end-piece, with a base forming longitudinal arches curved radially and supporting a central pellet which make between them, passageways open to a radial flow of the entering air leaving the drop dispensing head,
  through which the liquid is delivered under an effect of a pressure applied against said wall, in which said dispensing head is mounted in a sealed manner by the insert in a neck of the bottle, in communication with said reservoir, and in which the anti-bacterial filtering membrane, partially hydrophilic and partially hydrophobic, is mounted across said insert at the base of said end-piece, in order to allow the passage of the liquid in the direction of delivery and, in the reverse direction, the passage of air required to enter the bottle in compensation after a delivery of liquid, characterized in that the base of the insert ends inside said reservoir with arches providing passageways for a radial circulation of the air entering the bottle through said pad to the periphery of the reservoir,
  wherein the insert is mounted in the neck of the bottle with the base of the insert configured to extend beyond the neck and to a narrowing portion inclined toward the peripheral wall of the bottle so that the entering air, which is directed radially to the peripheral wall of the bottle by obstruction of the central pellet, is guided in a laminar flow along the said wall.

12. Drop dispensing head according to claim 1, wherein the longitudinal arches provide a space at the base of the insert configured to allow air to escape in a radial direction around said axis of the insert.

13. Drop dispensing head according to claim 12, wherein the space includes a volume of about 0.40 cm$^3$.

* * * * *